United States Patent [19]

Kadkhodayan

[11] Patent Number: 5,344,951
[45] Date of Patent: Sep. 6, 1994

[54] PRODUCTION OF ALKYL PHOSPHITES

[75] Inventor: Abbas Kadkhodayan, Collinsville, Ill.

[73] Assignee: Ethyl Petroleum Additives, Inc., Richmond, Va.

[21] Appl. No.: 31,838

[22] Filed: Mar. 16, 1993

[51] Int. Cl.$^5$ ............................................. C07F 9/142
[52] U.S. Cl. ...................................... 558/110; 558/214
[58] Field of Search .......................................... 558/110

[56] References Cited

U.S. PATENT DOCUMENTS 2,670,368  2/1954  Baker et al. ............................ 558/110
3,725,515  4/1973  Schimmelschmidt et al. ....... 558/10

*Primary Examiner*—Patricia L. Morris
*Assistant Examiner*—Michael G. Ambrose
*Attorney, Agent, or Firm*—John F. Sieberth

[57] ABSTRACT

This invention relates to an improved process for producing diesters of phosphorous acid. The process comprises (a) reacting phosphorous acid with monohydric alcohol in a petroleum distillate solvent while maintaining a reaction mass temperature within the range of from about 130° to about 138° C., and (b) refluxing the reaction mass during the reaction, wherein the phosphorous acid contains about 20 up to about 35 wt. % water, the molar ratio of alcohol to phosphorous acid used is within the range of from about 2.0:1 to about 4.0:1, and water is removed from the reaction mass essentially as it is formed during steps (b) and (c).

20 Claims, No Drawings

PRODUCTION OF ALKYL PHOSPHITES

FIELD

This invention relates to a cost-effective, commercially feasible process for preparing dihydrocarbyl esters of phosphorous acid.

BACKGROUND

Dihydrocarbyl esters of phosphorous acid, such as dibutyl hydrogen phosphite are useful as gear lubricant additives as is or they may be further reacted with elemental sulfur to form an intermediate reactive product. The intermediate reactive product can then be reacted with an amine, olefin, or alkylene oxide to obtain a desired lube oil additive.

Processes for preparing dihydrocarbyl phosphites are well known. Alkyl phosphites may be prepared by the reaction of alcohols and alkali metal alkoxides with phosphorus trichloride and with phosphorus trioxide. However, reactions of trivalent phosphorus derivatives are known to be more complex and more difficult to control than reactions involving the corresponding pentavalent phosphorus derivatives.

Baker, et al., U.S. Pat. No. 2,670,368 and GB Patent No. 699,154 disclose the direct esterification of phosphorous acid with monohydric alcohols. According to Baker, et al., alkyl phosphites, principally dialkyl phosphites, may be produced in good yield without the formation of excessive quantities of ethers, olefins, and other undesirable products by esterification of the alcohol with phosphorous acid under such conditions that the water present and formed during the esterification is removed continuously. Continuous removal of water is achieved by the use of a solvent which forms a ternary azeotropic mixture with water and the alcohol. The phosphorous acid used in the Baker, et al. process is obtained by concentrating a more dilute acid, for example, concentrating commercial 70 percent acid whereby a solid product containing 90 percent or more $H_3PO_3$ is usually formed.

THE INVENTION

Previously, it was believed that it was necessary to utilize concentrated or solid phosphorous acid whereby water is removed from the acid prior to initiation of the reaction between phosphorous acid and monohydric alcohol. It has now been discovered that phosphorous acid solutions containing more than about 10 up to about 35 wt. % water, preferably from about 20 to about 30 wt. %, can be reacted with monohydric alcohol without first concentrating the acid to 90 wt. % or more. This discovery has led to a dramatic decrease in reaction time, without adversely affecting the yield or purity of diester product thus produced. Accordingly, the reaction can be completed in as little as 4 to 10 hours in laboratory scale reactions. Previous attempts utilizing solid phosphorous acid or phosphorous acid which had been concentrated prior to reaction had been unsuccessful in obtaining the purity of product and shortened reaction time obtained by the present invention.

In one embodiment, this invention provides a method for producing a diester of phosphorous acid and a monohydric alcohol in high yield and high purity. The method comprises (a) charging phosphorous acid solution and solvent to a reaction vessel, wherein the phosphorous acid contains more than about 10 up to about 35 wt. % water; (b) feeding from about 2.0 to about 4.0 moles of monohydric alcohol per mole of phosphorous acid to the reaction vessel containing phosphorous acid solution and solvent while maintaining a reaction mass temperature within the range of from about 130° to about 138° C. and while removing water from the reaction mass essentially as it is formed; and (c) subsequently, separating alcohol and solvent from the dihydrocarbyl phosphite formed in step (b).

In another embodiment, this invention relates to an improvement in a process for producing dialkyl esters of phosphorous acid. The improvement comprises (a) charging phosphorous acid solution and a petroleum distillate solvent to a reaction vessel, (b) reacting the phosphorous acid with monohydric alcohol in the solvent while maintaining a reaction mass temperature within the range of from about 130° to about 138° C., and (c) refluxing the reaction mass during the reaction, wherein the phosphorous acid contains more than about 10 up to about 35 wt. % water, the molar ratio of alcohol to phosphorous acid used is within the range of from about 2.0:1 to about 4.0, and water is removed from the reaction mass essentially as it is formed during steps (b) and (c).

Prior to initiating the esterification reaction, phosphorous acid and solvent are charged to the reaction vessel. Phosphorous acid is obtained commercially as about 65-75 wt. % aqueous acid solution. Typical impurities which may be present in commercially available phosphorous acid include, water (25 to 35 wt. %), acetic acid (<1 wt. %), HCl (10-2000 ppm), iron (0-10 ppm) and 1-hydroxyethylidene diphosphonic acid (0-5 wt. %). In the alternative, relatively pure phosphorous acid containing more than about 10 up to 35 weight percent water may be used.

A key feature of this invention is the reaction of phosphorous acid solution containing more than about 10 up to about 35 wt. % water, preferably from about 20 to about 30 wt. % water, without the need to first concentrate the acid to 90 wt. % or more. Water is not only present in the phosphorous acid when the reaction is initiated, but during the reaction water is formed as the monohydric alcohol and phosphorous acid react to form the diester product. Water also forms as a result of side reactions such as the formation of dihydrocarbyl ethers and pyrophosphorous acid, and the dehydration of the alcohols. By removing water from the reaction vessel essentially as it is formed, the reaction is driven to completion. While not desiring to be bound by theory, it is believed that if too much water is present in the reaction mass, inhibition of completion of the reaction will occur according to the following equilibrium limiting overall reaction for dialkyl esters of phosphorous acid:

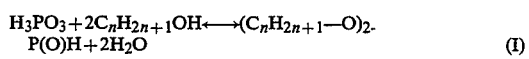

$$H_3PO_3 + 2C_nH_{2n+1}OH \leftrightarrow (C_nH_{2n+1}-O)_2P(O)H + 2H_2O \qquad (I)$$

wherein n is an integer from 1 to 8; and for dialkenyl esters of phosphorous acid:

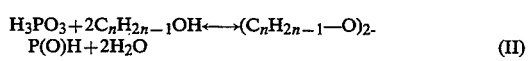

$$H_3PO_3 + 2C_nH_{2n-1}OH \leftrightarrow (C_nH_{2n-1}-O)_2P(O)H + 2H_2O \qquad (II)$$

wherein n is an integer from 2 to 8.

It has been discovered, quite surprisingly, that the water initially present in the phosphorous acid reactant has little or no effect on the purity and yield of product thus obtained. Accordingly, it is now possible, to eliminate the preconcentration step for the phosphorous acid prior to initiating the esterification reaction. By elimination of the preconcentration step, the reaction cycle can be shortened considerably resulting in a reduction in the cost of preparing diesters of phosphorous acid. Further, the invention enables greater plant production capacity and throughput from a given sized facility.

The monohydric alcohols useful in preparing the diesters of this invention may be selected from monohydric aliphatic alcohols having from 1 to 8 carbon atoms, such as propyl, isopropyl, n-butyl, 2-methyl-1-propyl, amyl, isoamyl, n-hexyl, n-heptyl, n-octyl, 2-ethylhexyl, 1,3-dimethylbutyl, allyl, 3-buten-1-ol, crotyl, alcohols, and the like, or mixtures thereof. Preferred monohydric aliphatic alcoholic reactants are the alkyl alcohols (alkanols) having from 3 to 8 carbon atoms, most preferably, n-butanol and 2-methyl-1-propanol. Monohydric alcohols such as n-butanol and 2-methyl-1-propanol are commercially available in relatively pure form, i.e. 99 wt. % purity or greater. Less pure monohydric alcohols may also be used. However, lower purity alcohols are less desirable due to the formation of byproducts which may effect the product yield and purity thus obtained.

The ratio of monohydric alcohol to phosphorous acid is a critical feature of the process of this invention. For the preparation of diesters of phosphorous acid, it is preferred to use a stoichiometric excess of monohydric alcohol based on the total moles of phosphorous acid used, i.e. more than 2.0 moles of alcohol per mole of acid. More preferably, the molar ratio of monohydric alcohol to acid ranges from about 2.2 to about 4.0 moles of alcohol per mole of phosphorous acid. Most preferably, the molar ratio of alcohol to acid ranges from about 2.5:1 to about 3.0:1.

The solvent useful in the process of this invention may be one or a mixture of solvents having a boiling point within the range of from about 100° to 160° C., more preferably, from about 110° to about 150° C., and most preferably from about 118° to about 150° C. Such a solvent or solvent mixture may be obtained from a petroleum distillate fraction having a boiling point within the desired range. A useful solvent may be selected from n-octane; toluene; o-, m-, or p-xylene; o-, m-, or p-dimethylcyclohexane; dibutyl ether; naphtha; ISOPAR® E (from Exxon Chemical Company) and the like, or mixtures of any two or more of the foregoing. Particularly preferred solvents are paraffinic solvents such as naphtha and n-octane, most preferably VM&P (Varnish Makers' and Painters') naphtha having a boiling point range within the range of from about 118° to about 150° C.

The amount of solvent used is not critical to the invention and is related to the amount of phosphorous acid (based on 100 wt. % dry acid) charged to the reaction vessel. Accordingly, the solvent is present in a weight ratio of from about 0.5:1 to about 1.5:1 solvent to 100 wt. % dry acid. More or less solvent can be used, however, for increased yields and reaction efficiency, it is most desirable to use a solvent to acid weight ratio of from about an 0.8:1 to about 1.2:1.

During the reaction of monohydric alcohol with phosphorous acid, it is highly desirable to maintain the reaction temperature within the range of from about 130° to about 138° C., more preferably, from about 130° to about 136° C., and most preferably, from about 131° to about 136° C. In order to maintain the reaction temperature within the desired range, the monohydric alcohol is desirably charged to the reaction vessel in multiple portions. For example, the alcohol may be charged to the reaction vessel in two portions wherein about one third to about one half of the total amount of monohydric alcohol to be used is initially fed to the reaction vessel after charging the phosphorous acid and solvent to the reaction vessel. During the reaction, a second portion of monohydric alcohol is fed to the reaction vessel at a rate sufficient to maintain the temperature within the desired range. The second portion of monohydric alcohol is the remaining two thirds to one half of the total monohydric alcohol used, which second portion may be fed in all at once, or over a period of time in order to control the reaction mass temperature. While the use of multiple portions of alcohol feed to the reaction vessel is beneficial to maintaining the desired reaction temperature, this invention is not limited to such a means for controlling the reaction temperature. Accordingly, the total amount of alcohol to be reacted may be fed to the reaction vessel all at once, provided adequate control of the reaction mass temperature can be maintained throughout substantially the entire reaction period.

The reaction is maintained at the desired reaction temperature for 4 hours or more depending on the amount of reactants and the scale of reaction used. Typically, the reaction will be complete in 8 to 10 hours for laboratory scale reactions. An indication of the near completion of the reaction is the rate of water removal from the reaction mass. As the reaction nears completion, less water is being formed, and thus less water is available for removal from the reaction mass. Accordingly, it has been found that a high yield of diester product can be recovered from the reaction mass when the rate of water removal from the reaction mass has decreased to less than 0.1 mole of water per hour per mole of phosphorous acid charged to the reaction vessel. Continuation of the reaction beyond this point may result in the undesirable formation of dihydrocarbyl ether which can contaminate the product.

Pressure is not critical to the invention. Accordingly, the reaction may be conducted at pressures ranging from subatmospheric to superatmospheric. It is most desirable to utilize atmospheric pressure during the esterification reaction for ease of equipment design and operation.

Once the reaction is complete, the diester product of phosphorous acid may be recovered utilizing conventional vacuum distillation techniques to remove water, solvent, and unreacted monohydric alcohol from the reaction mass. When VM&P naphtha is the solvent, a particularly useful method of recovering the diester product is to heat the reactor to a temperature sufficient to vaporize at least a portion of the solvent and excess monohydric alcohol while partially condensing the resulting vapors with reflux back to the reaction vessel. The cooling medium for the partial condenser is preferably maintained at a temperature of about 45° C. during the removal of the monohydric alcohol and solvent from the reaction mass. The pressure during the solvent removal step is typically maintained at about 29 inches of mercury vacuum during solvent removal. By utilizing a partial condenser, recovery of product having a purity of 99 wt. % or more can be obtained. It has been found, unexpectedly, that by using the partial condenser to reflux reaction mass vapors containing diester product during the solvent removal step, there is a reduced need for the use of a separate distillation column to purify the product.

After removal of the solvent, the reaction mixture contains diester of phosphorous acid and a heel containing impurities. The diester of phosphorous acid may be recovered by heating the solventless reaction mixture to a temperature sufficient to strip the diester product from the reaction mixture. It has been found advantageous not to strip all of the diester of phosphorous acid from the reaction mixture. In this regard, there remains a heel of reaction material containing a major amount of monoalkyl or monoalkenyl hydrogen phosphite and a minor amount of impurities which may include pyrophosphorous acid, phosphorous acid, dialkyl or dialkenyl hydrogen phosphite, phosphoric acid, 1-hydroxyethylidene diphosphonic acid and polyphosphates. By minor amounts is meant less than about 25 wt. % based on the total weight of heel. This heel containing monobutylated species and impurities can be used in subsequent runs whereby the yield based on acid charged to the reaction vessel is about 100%. By utilizing the methods described herein, the heel containing impurities can be used without removal for 10 or more subsequent runs. During the subsequent runs, the buildup of significant amounts of impurities in the recycled material has been found to be negligible.

In order to illustrate the features of this invention, the following Examples 1-3 are given.

EXAMPLE 1

Preparation of Dibutyl Hydrogen Phosphite

The reaction equipment used in these examples includes a 1 liter flask equipped with an agitator, thermometer, and two sets of reflux condensers (a partial condenser with the cooling medium being maintained at 45° C. and an ethylene glycol condenser being maintained at −10° C. for solvent condensation), a Dean-Stark moisture trap, and a return line to the reaction flask. To the reaction flask were added 163.3 grams of 75 wt. % phosphorous acid (1.5 mole of pure acid), 92.4 grams butanol (1.24 moles) and 123 grams of VM&P naphtha. The reaction flask contents were heated to initiate the reaction and water was removed from the phosphorous acid reactant and from the reaction mass as it was formed. When the reaction flask contents reached 136° C., a second portion of butanol (184.8 grams) was added using an addition funnel in 15 mL increments so as to maintain the reaction mass temperature of 135° C. The reaction mass was maintained at 134° to 136° C. by feeding the second portion of butanol to the flask at a slow rate. After completion of the butanol feed, the addition funnel was replaced with a thermometer. The reaction mass was agitated at 600 RPM and refluxed for 9 hours while collecting water essentially as it was formed. The overall reaction rate for 8 hours of reaction, in terms of water removal rate was 0.206 moles H₂O per hour removed per mole of phosphorous acid charged. At the end of the nine hour period, heating of the reaction mass was discontinued and a reduced pressure was applied. The pressure was maintained at 27 inches of mercury, and the reaction mass temperature was maintained at about 65° to 75° C. resulting in removal of most of the solvent and excess butanol. The residue remaining in the reaction flask was then heated to 90° C. and the pressure decreased to 27.5 to 29 inches of mercury vacuum. At this reduced pressure, the naphtha and butanol began condensing in the glycol condenser which was cooled to −10° C. while dibutyl hydrogen phosphite was condensing in the partial condenser and being refluxed to the reaction flask. When the contents of the reaction flask reached 118° C., dibutyl hydrogen phosphite was collected in the Dean-Stark trap until the temperature of the contents of the flask obtained 190° C. Then the reaction flask was pressurized to atmospheric pressure using nitrogen and the reaction system was purged with nitrogen to remove any phosphine residue which may have formed. Upon completion of the reaction and recovery of the product, 232 grams of dibutyl hydrogen phosphite having a purity of 99 GC area % was obtained. Based on the amount of pure phosphorous acid charged to the reaction flask, the actual yield of dibutyl hydrogen phosphite was 80%. Remaining in the flask at the conclusion of the reaction and product recovery step was a heel containing monobutylated hydrogen phosphite, and byproducts from the production of dibutyl hydrogen phosphite.

EXAMPLE 2

Preparation of Dibutyl Hydrogen Phosphite

In this example, n-octane having a boiling point of 125°-127° C. was used as the solvent. The general procedure of Example 1 was followed with the exception that reaction temperature was maintained at about 131° C. The yield of dibutyl hydrogen phosphite was 84.6% having a purity of 99.59 GC area %. The overall rate of water removal during the reaction was 0.202 moles H₂O per hour removed per mole of phosphorous acid charged the reaction vessel.

In the next examples, the heel from a previous run containing monobutylated hydrogen phosphite and byproducts was used to demonstrate the high yield of product obtained without a substantial increase in impurities in the product.

EXAMPLE 3

Preparation of Dibutyl Hydrogen Phosphite Without Removing Heel

The general procedure of Example 1 was followed for run 1 with the exception that the heel (about 30 grams) from a previous run was not removed from the reaction flask prior to charging fresh phosphorous acid, n-butanol and solvent to the flask. The heel remaining in the reaction flask contained unreacted phosphorous acid, monobutylated hydrogen phosphite, pyrophosphorous acid, 1-hydroxyethylidene diphosphonic acid and dibutyl hydrogen phosphite. Run 2 utilized the heel from run 1, and run 3 utilized the heel from run 3. Results of these runs are given in the following Table I.

TABLE I

| Run No. | Solvent | DBHP yield (%) | DBHP purity (GC area %) | Reaction Time (hours) |
|---|---|---|---|---|
| 1 | VM & P Naphtha | 99.8 | 99.35 | 9.13 |
| 2 | VM & P Naphtha | 96.6 | 99.30 | 9.22 |
| 3 | VM & P Naphtha | 99.3 | 99.29 | 9.22 |

The next series of runs are not of this invention, but are given for comparison purposes.

EXAMPLE 4

Preparation of Dibutyl Hydrogen Phosphite (Comparative Example)

In these runs, the general procedure of Example 1 was followed with the exception that various solvents and reaction temperatures were used. In run number 7, the reaction was conducted without the use of a partial condenser to reflux the reaction mass in the reaction vessel during the reaction and solvent stripping steps. The results of runs 4–7 are given in Table II.

TABLE II

| Run No. | Solvent | Reaction Temperature (°C.) | DBHP yield (%) | DBHP purity (GC area %) | Overall Water Removal Rate[1] |
|---|---|---|---|---|---|
| 4 | toluene | 127 | 79.16 | 98.73 | 0.196 |
| 5 | ISOPAR ® E | 123 | 68.26 | 98.93 | 0.185 |
| 6 | dibutyl ether | 142 | 64.74 | 98.82 | 0.155 |
| 7 | xylene | 140 | 53.74 | 77.22 | 0.155 |

[1] moles of $H_2O$ per hour per mole of phosphorous acid charged

Variations in the invention are within the spirit and scope of the appended claims.

What is claimed is:

1. A method for producing diesters of phosphorous acid comprising:
   a) charging phosphorous acid solution and solvent to a reaction vessel, wherein the phosphorous acid contains about 20 up to about 35 wt. % water;
   b) feeding from about 2.0 to about 4.0 moles of monohydric alcohol per mole of phosphorous acid to the reaction vessel containing phosphorous acid solution and solvent while maintaining a reaction mass temperature within the range of from about 130° to about 138° C. and while removing water from the reaction mass essentially as it is formed; and
   c) subsequently, separating alcohol and solvent from the dihydrocarbyl phosphite formed in step (b).

2. The method of claim 1 wherein the solvent is a paraffinic solvent.

3. The method of claim 2 wherein the solvent is VM&P (Varnish Makers' & Painters') naphtha having a boiling point within the range of from about 118° to about 150° C.

4. The method of claim 2 wherein the solvent is n-octane having a boiling point within the range of from about 125° to about 127° C.

5. The method of claim 1 further comprising refluxing the reaction mass during step (b).

6. The method of claim 1 wherein the weight ratio of solvent to anhydrous phosphorous acid charged to the reaction vessel ranges from about 0.8:1 to about 1.2:1.

7. The method of claim 1 wherein the monohydric alcohol is n-butanol.

8. The method of claim 1 wherein the monohydric alcohol is isobutanol.

9. The method of claim 1 wherein the molar ratio of monohydric alcohol to phosphorous acid ranges from about 2.5:1 to about 3.2:1.

10. The method of claim 1 further comprising feeding the monohydric alcohol to the reaction vessel in multiple portions so as to maintain the reaction mass temperature within the range of from about 131° to about 136° C.

11. The method of claim 1 wherein, prior to charging phosphorous acid and solvent, the reaction vessel contains a heel from a previous reaction wherein the heel contains diester of phosphorous acid and a minor amount of impurities.

12. A process for producing dialkyl esters of phosphorous acid, comprising (a) charging phosphorous acid solution and a petroleum distillate solvent to a reaction vessel, (b) reacting the phosphorous acid with monohydric alcohol in the solvent while maintaining a reaction mass temperature within the range of from about 130° to about 138° C., and (c) refluxing the reaction mass during the reaction, wherein the phosphorous acid contains about 20 up to about 35 wt. % water, the molar ratio of alcohol to phosphorous acid used is within the range of from about 2.0: 1 to about 4.0: 1, and water is removed from the reaction mass essentially as it is formed during steps (b) and (c).

13. The process of claim 12 wherein the solvent is a paraffinic solvent.

14. The process of claim 13 wherein the paraffinic solvent is Varnish Makers' and Painters' naphtha having a boiling point within the range of from about 118° to about 150° C.

15. The process of claim 13 wherein the paraffinic solvent is n-octane having a boiling point within the range of from about 125° to about 127° C.

16. The process of claim 14 wherein the weight ratio of solvent to anhydrous phosphorous acid in the reaction mass ranges from about 0.8:1 to about 1.2:1.

17. The process of claim 16 wherein the monohydric alcohol is n-butanol.

18. The process of claim 16 wherein the monohydric alcohol is isobutanol.

19. The process of claim 17 wherein the molar ratio of monohydric alcohol to phosphorous acid ranges from about 2.5:1 to about 3.2:1.

20. The process of claim 19 wherein, prior to charging the reaction vessel with phosphorous acid and solvent, the reaction vessel contains a heel from a previous reaction wherein the heel contains diester of phosphorous acid and a minor amount of impurities.

* * * * *